(12) United States Patent
Fearnot et al.

(10) Patent No.: US 7,485,138 B2
(45) Date of Patent: Feb. 3, 2009

(54) TUBULAR GRAFT CONSTRUCT

(75) Inventors: Neal E. Fearnot, West Lafayette, IN (US); Michael C. Hiles, Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 0 days.

(21) Appl. No.: 10/068,212

(22) Filed: Feb. 6, 2002

(65) Prior Publication Data

US 2003/0026787 A1 Feb. 6, 2003

Related U.S. Application Data

(63) Continuation of application No. PCT/US00/21546, filed on Aug. 7, 2000.

(60) Provisional application No. 60/147,647, filed on Aug. 6, 1999.

(51) Int. Cl.
*A61F 2/06* (2006.01)

(52) U.S. Cl. .................. 623/1.1; 623/917; 623/921; 623/1.44

(58) Field of Classification Search .......... 623/1.1–1.54, 623/2.12–2.16, 917, 921; 606/151–156
See application file for complete search history.

(56) References Cited

U.S. PATENT DOCUMENTS

| | | | |
|---|---|---|---|
| 2,127,903 A | 8/1938 | Bowen | |
| 3,562,820 A | 2/1971 | Bernhard | |
| 4,502,159 A | 3/1985 | Woodroof et al. | |
| 4,902,508 A | 2/1990 | Badylak et al. | |
| 5,141,747 A | 8/1992 | Scholz | |
| 5,275,826 A | 1/1994 | Badylak et al. | |
| 5,281,422 A | 1/1994 | Badylak et al. | |
| 5,372,821 A | 12/1994 | Badylak et al. | |
| 5,460,962 A | 10/1995 | Kemp | |
| 5,527,355 A * | 6/1996 | Ahn ..................... | 623/1.36 |
| 5,554,389 A | 9/1996 | Badylak et al. | |
| 5,618,299 A * | 4/1997 | Khosravi et al. .......... | 623/1.2 |
| 5,674,242 A | 10/1997 | Phan et al. | |
| 5,693,085 A | 12/1997 | Buirge et al. | |
| 5,755,791 A | 5/1998 | Whitson et al. | |
| 5,763,416 A | 6/1998 | Bonadio et al. | |
| 5,885,619 A | 3/1999 | Patel et al. | |
| 5,910,168 A * | 6/1999 | Myers et al. ............ | 623/1.44 |
| 5,955,110 A | 9/1999 | Patel et al. | |
| 5,984,963 A | 11/1999 | Ryan et al. | |
| 6,027,779 A | 2/2000 | Campbell et al. | |
| 6,099,567 A | 8/2000 | Badylak et al. | |

(Continued)

FOREIGN PATENT DOCUMENTS

WO  WO 9825543  * 6/1998

*Primary Examiner*—Corrine McDermott
*Assistant Examiner*—Cheryl Miller
(74) *Attorney, Agent, or Firm*—Woodard, Emhardt, Moriarty, McNett & Henry LLP

(57) ABSTRACT

Described are medical devices which are or can be used to form tubular medical devices, and related methods. Preferred devices include tubular grafts of biomaterial having lumen walls which present no seam edge that traverses the entire length of the lumen, illustratively including devices having lumen walls which have a discontinuous seam presenting multiple seam edges. Such a device may include a tubular structure formed by inserting a plurality of extensions of a biomaterial sheet through a plurality of corresponding apertures of the sheet.

21 Claims, 9 Drawing Sheets

U.S. PATENT DOCUMENTS

| | | |
|---|---|---|
| 6,187,039 B1 | 2/2001 | Hiles et al. |
| 6,206,931 B1 | 3/2001 | Cook et al. |
| 6,240,968 B1 * | 6/2001 | Bigonzi-Jaker et al. ..... 138/115 |
| 6,475,232 B1 | 11/2002 | Babbs et al. |
| 6,666,882 B1 * | 12/2003 | Bose et al. .................. 623/1.15 |
| 6,669,719 B2 * | 12/2003 | Wallace et al. ............. 623/1.12 |
| 6,949,119 B2 * | 9/2005 | Myers ........................ 623/1.13 |

\* cited by examiner

TUBULAR GRAFT CONSTRUCT

RELATED APPLICATION

The present application is a continuation of International Patent Application No. PCT/US00/21546 filed Aug. 7, 2000 designating the United States and published in English, which claims the benefit of U.S. Provisional Patent Application, Ser. No. 60/147,647, filed Aug. 6, 1999, each of which is hereby incorporated by reference in its entirety.

TECHNICAL FIELD

The invention relates generally to a medical device, and more particularly, to a tubular graft biomaterial device.

BACKGROUND OF THE INVENTION

It has become common to treat a variety of medical conditions by introducing an implantable medical device into the alimentary, circulatory, coronary, urological, renal, and other organ systems. For example, coronary vessels via delivery catheters, such as balloon catheters.

In the case of aneurysm treatment, an aneurysm is caused by a weakening of the vessel wall, which causes an invagination of the vessel wall. Blood flow is inhibited at the neck of the aneurysm due to turbulence caused by blood entering and exiting the lumen of the aneurysm. Current medical treatment of aneurysms include the use of metal coils, such as the FDA approved Gugliemi Detachable Coil, inserted into the lumen of the aneurysm. However, this platinum coil is relatively soft and does not provide a complete packing of the aneurysm lumen. It is not uncommon for the aneurysm to re-canalize, enlarge, and even rupture. The heavy metal used in the coils provide the necessary radiographic visualization to ensure that the coils are localized properly and whether, during a subsequent examination, the coils remain in the situs.

However, there are problems associated with using synthetic materials, which include thrombus formation, immune response leading to rejection, and undesired occlusion of the vessel. Therefore, a better material for implantation in any application, such as coronary, vascular, body wall repair, orthopaedic, tissue graft, dermal, and other industries is needed. One such material is a newly discovered biomaterial comprising tissue mucosa, tissue serosa, or tissue submucosa.

Tissue implants in a purified form and derived from collagen-based materials have been manufactured and disclosed in the literature. Cohesive films of high tensile strength have been manufactured using collagen molecules or collagen-based materials. Aldehydes, however, have been generally utilized to cross-link the collagen molecules to produce films having high tensile strengths. With these types of materials, the aldehydes may leech out of the film, e.g. upon hydrolysis. Because such residues are cytotoxic, the films are poor tissue implants.

Other techniques have been developed to produce coliagen-based tissue implants while avoiding the problems associated with aldehyde cross-linked collagen molecules. One such technique is illustrated in U.S. Pat. No. 5,141,747 wherein the collagen molecules are cross-linked or coupled at their lysine epsilon amino groups followed by denaturing the coupled, and preferably modified, collagen molecules. The disclosed use of such collagen material is for tympanic membrane repair. While such membranes are disclosed to exhibit good physical properties and to be sterilized by subsequent processing, they are not capable of remodeling or generating cell growth or, in general, of promoting regrowth and healing of damaged or diseased tissue structures.

In general, researchers in the surgical arts have been working for many years to develop new techniques and materials for use as implants to replace or repair damaged or diseased tissue structures, for example, blood vessels, aneurysms, muscle, ligaments, tendons and the like. It is not uncommon today, for instance, for an orthopedic surgeon to harvest a patellar tendon of autogenous or allogenous origin for use as a replacement for a torn cruciate ligament. The surgical methods for such techniques are known. Further, it has been common for surgeons to use implantable prostheses formed from plastic, metal and/or ceramic material for reconstruction or replacement of physiological structures. Despite their wide use, surgical implanted prostheses present many attendant risks to the patient.

Researchers have also been attempting to develop satisfactory polymer or plastic materials to serve as functional tissue structures and/or other connective tissues, e.g., those involved in hernia and joint dislocation injuries. It has been discovered that it is difficult to provide a tough, durable plastic material which is suitable for long term connective tissue replacement. The tissues surrounding the plastic material can become infected and difficulties in treating such infections often lead to the failure of the implant or prostheses.

As mentioned above, various collagen-based materials have also been utilized for the above-mentioned tissue replacements; however, these materials either did not exhibit the requisite tensile strength or also had problems with infection and other immunogenic responses, encapsulation, or had other problems. In a related patent, U.S. Pat. No. 5,372,821, it is disclosed that a submucosa collagenous biomaterial may be sterilized by conventional techniques, e.g., aldehyde tanning, propylene oxide, gamma radiation and peracetic acid. No specific processing steps are disclosed except that the submucosa layer is first delaminated from the surrounding tissue prior to sterilization treatment.

Some materials considered desirable are biological materials (biomaterials) from autogenous, allogenous, or xenogeneic (heteroplastic) sources. Biomaterials are desirable as they can be malleable and less likely to be rejected as foreign. One such biomaterial is collagen. Collagen is a protein molecule that comes in many types. For example, collagen Type I constitutes a significant amount of the collagen in the body. Type I is a heterotrimeric molecule, has a helical configuration, and is characterized by a Glycine-X-Y amino acid repeating sequence. Due to its abundance in the human body, collagen is being examined for its uses in medical treatment.

One of the problems associated with biomaterials includes leakage or seepage from the tubular graft. Particularly, a graft made by suturing two ends of a flat sheet together cause holes to extend from the lumenal side to the outside, thus providing small channels for lumenal fluid to seep. A reduced seepage biomaterial construct is desired and would be well-received.

Problems associated with synthetic grafts are well-documented. For example, it is known that the mechanical properties of synthetic grafts degrade over time, as described in Vinard et al, Stability of Performances of Vascular Prostheses Retrospective Study of 22 Cases of Human Implanted Prostheses, Vol. 22(7) Jour. of Biomedical Materials Research pg. 633-648(July 1988); and Manfredi et al., Vascular Prostheses, vol. 12(3) Emergency Medicine Clinics of North America pg. 657-77 (August 1994). A graft that gets stronger over time is more desirable than one that degrades over time.

One other problem associated with synthetic or biomaterial grafts include the occlusion of the lumen itself. Often times, the graft materials come loose or the layers comprising the graft separate, thus causing material to hang into the lumen. This debris causes thrombogenesis and reduces patency of the graft. If the thrombus were to dislodge, disastrous effects will soon follow.

SUMMARY OF THE INVENTION

The foregoing problems are solved and a technical advance is achieved in a newly discovered graft construct comprising a biomaterial. One exemplary biomaterial is a newly discovered collagenous material called tela submucosa, which has been shown to be a remarkable biomaterial that promotes remodeling of the surrounding tissue, such as cellular invasion, host incorporation, and absorption of the tela submucosa material into the local tissue. One exemplary tela submucosa is small intestine submucosa (SIS). Furthermore, SIS has been shown to be acellular, strong, and exhibit a sidedness in that it has a differential porosity of its mucosal and serosal sides. Highly purified SIS also does not trigger any negative immune system response as evidence suggests that it has no viral activity when checking for enveloped, non-enveloped, DNA, and RNA virus. Studies also show that SIS increases the Th-2 immune response by increasing the production of interleukin-10 over interferon-γ, which indicates that the immune response is more accommodation than rejection. Due to these and other properties, SIS makes for an excellent implantable biomaterial for use in multiple industries.

While collagenous biomaterials are known in the industries, none speak to the collagenous biomaterial being reduced in seepage or leakage properties. As mentioned above a tubular graft comprising a biomaterial that has its manufacturing holes sealed or covered over provides increased structural integrity and reduced seepage from the tube.

In accordance with the present invention, provided is a collagenous implantable biomaterial (including a collagenous extracellular matrix), such as tela submucosa, such as small intestine submucosa (SIS) that is further advantageous in that it is created in such a manner to reduce seepage. Further provided in accordance with the present invention is the biocompatibility of the present device over other presently available biomaterials. The present invention further comprises a collagenous biomaterial that has an endotoxin level of less than 12 endotoxin units per gram. Advantageously, the present invention permits capitalization of the newly discovered collagenous biomaterial and its biotropic properties to be combined with vessel graft constructs. This permits further industrial application of the disclosed medical device.

DETAILED DESCRIPTION

In the discussions herein, a number of terms are used. In order to provide a clear and consistent understanding of the specification and claims, the following definitions are provided.

Bioburden—refers to the number of living microorganisms, reported in colony-forming units (CFU), found on and/or in a given amount of material. Illustrative microorganisms include bacteria, fungi and their spores.

Disinfection—refers to a reduction in the bioburden of a material.

Sterile—refers to a condition wherein a material has a bioburden such that the probability of having one living microorganism (CFU) on and/or in a given section of the material is one in one-million or less.

Pyrogen—refers to a substance which produces febrile response after introduction into a host.

Endotoxin—refers to a particular pyrogen which is part of the cell wall of gram-negative bacteria. Endotoxins are continually shed from the bacteria and contaminate materials.

Purification—refers to the treatment of a material to remove one or more contaminants which occur with the material, for instance contaminants with which the material occurs in nature, and/or microorganisms or components thereof occurring on the material. Illustratively, the contaminants may be those known to cause toxicity, infectivity, pyrogenicity, irritation potential, reactivity, hemolytic activity, carcinogenicity and/or immunogenicity.

Biocompatibility—refers to the ability of a material to pass the appropriate or relevant biocompatibility test or tests set forth in International Standards Organization (ISO) Standard No. 10993, or the U.S. Pharmacopeia (USP) 23, or the U.S. Food and Drug Administration (FDA) blue book memorandum No. G95-1, entitled "Use of International Standard ISO-10993, Biological Evaluation of Medical Devices Part-1: Evaluation and Testing." Typically, these tests assay as to a material's toxicity, infectivity, pyrogenicity, irritation potential, reactivity, hemolytic activity, carcinogenicity and/or immunogenicity. A biocompatible structure or material when introduced into a majority of patients will not cause an adverse reaction or response. In addition, it is contemplated that biocompatibility can be effected by other contaminants such as prions, surfactants, oligonucleotides, and other biocompatibility effecting agents or contaminants.

Contaminant—refers to an unwanted substance on, attached to, or within a material. This includes, but is not limited to: bioburden, endotoxins, processing agents such as antimicrobial agents, blood, blood components, viruses, DNA, RNA, spores, fragments of unwanted tissue layers, cellular debris, and mucosa.

Tela submucosa—refers to a layer of collagen-containing connective tissue occurring under the mucosa in most parts of the alimentary, respiratory, urinary, integumentary, and genital tracts of animals.

Includes—refers to a list of items included but does not limit the list, e.g., such as but is not limited to, the following items . . .

Figure 1:
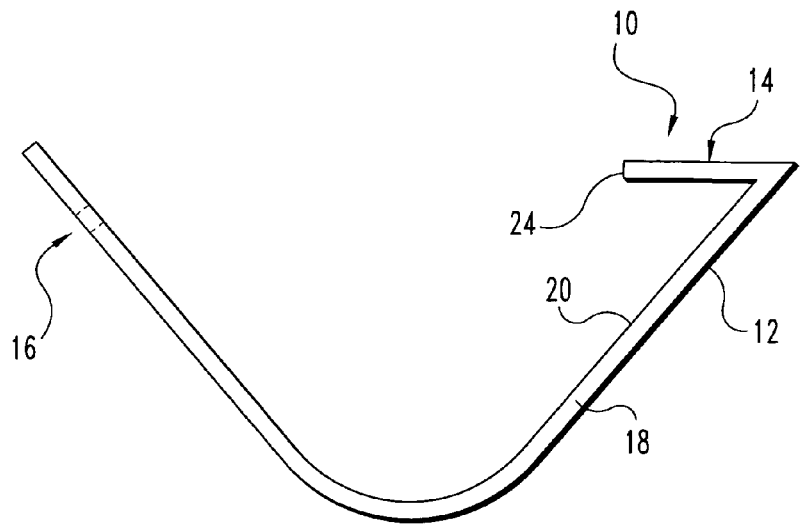
FIG. 1 represents an end view of the biomaterial.
Figure 2:
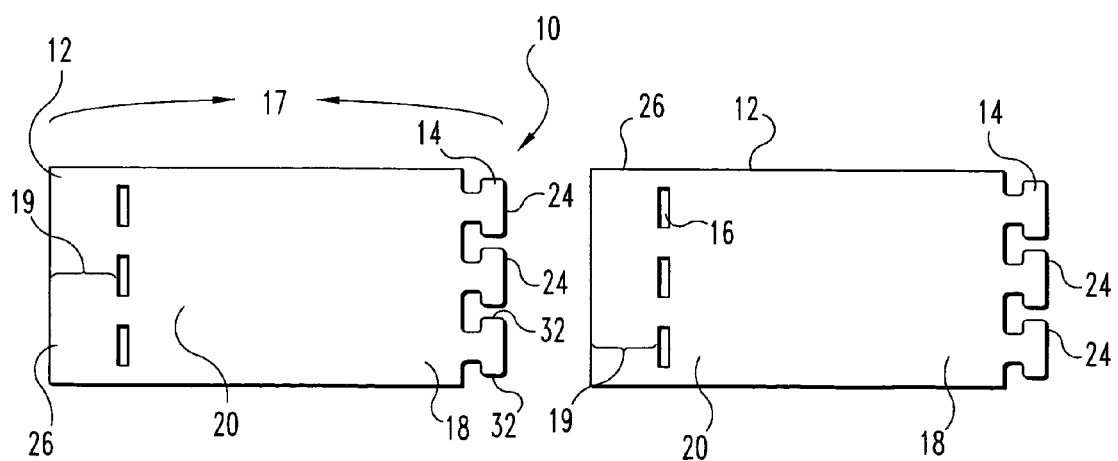
FIG. 2 represents a top down view of the flat biomaterial.

With reference to FIGS. 1 and 2, the graft 10, initially starts off as a flat sheet. The flat sheet generally comprises a first biomaterial 12 such as, but not limited to, at least one of a submucosal tissue, mucosal tissue, serosal tissue, collagen, partially collagenous biomaterial, elastin, polytetraflouroethylene, polyester, stainless steel, DACRON(R), ORLON (R), FORTISAN (R), nylon, polypropylene, polyglactin 910, polyglycolic acid, pericardium, dura tissue, facia lata, a biocompatible material, a synthetic material, polymers, polypyrramidole, co-polymers, and/or any combination or part thereof. One such first biomaterial 12 includes collagenous biomaterial, such as tissue mucosa or tela submucosa which also further includes a tissue submucosa, which further includes a small intestine submucosa (SIS). It is understood that any reference to tela submucosa also includes tissue mucosa or tissue serosa. Tela submucosa is a multi-laminate structure, comprising the tunica submucosa, lamina muscularis mucosa, and the stratum compactum. Tela submucosa has biotropic agents comprising at least one of a proteoglycan glycosaminoglycan, and growth factor. The tela submucosa can be made using the techniques described in Cook et al., WIPO Publication WO 98/22158, dated 28 May 1998, which is the published application of PCT/US97/14855, the disclosure of which is set forth below. Tela submucosa is a decellularized or acellular tissue, which means it is devoid of intact viable cells, although some cell components may remain in the tissue. All types of collagenous materials, as are any type of biocompatible synthetic materials, are contemplated herein. For example, included herein are: gastric submucosa as described in PCT/US97/22729, published as WO 98/26291; liver tissue as described in PCT/US97/22727, published as WO 98/25637; stomach tissue as described in PCT/US97/23010, published as WO 98/25636; and urinary tissue as described in U.S. Pat. No. 5,554,389, issued to Badylak et al., and bovine serosa.

One type of biomaterial is mucosa, such as tela submucosa, and as with many animal tissues, is generally aseptic in its natural state, provided the human or animal does not have an infection or disease. This is particularly the case since the tela submucosa is an internal layer within the alimentary, integumentary, respiratory, urinary, and genital tracts of animals. Accordingly, it is generally not exposed to bacteria and other cellular debris such as the epithelium of the intestinal tract. One feature of the present invention is the discovery that by disinfecting the source tissue for the tela submucosa prior to delamination, the aseptic state of the tela submucosa layer can be preserved or substantially preserved, particularly if the delamination process occurs under sterile conditions.

In particular, it has been discovered that disinfecting the tela submucosa source, followed by removal of a purified biomaterial including the tela submucosa, e.g. by delaminating the tela submucosa from the tunica muscularis and the tunica mucosa; minimizes the exposure of the tela submucosa to bacteria and other contaminants. In turn, this enables minimizing exposure of the isolated tela submucosa biomaterial to disinfectants or sterilants if desired, thus substantially preserving the inherent biochemistry of the tela submucosa and many of the tela submucosa's beneficial effects.

A tela submucosa implantable collagen biomaterial according to the present invention can, as indicated above, be obtained from the alimentary, respiratory, urinary, integumentary, or genital tracts of animals. Preferably, the tela submucosa tissues, which are collagen-based and thus predominantly collagen, are derived from the alimentary tract of mammals, such as cows, sheep, dogs, and most preferably from the intestinal tract of pigs. A most preferred source of whole small intestine is harvested from mature adult pigs weighing greater than about 450 pounds. Intestines harvested from healthy, non-diseased animals will contain blood vessels and blood supply within the intestinal tract, as well as various microbes such as $E.\ coli$ contained within the lumen of the intestines. Therefore, disinfecting the whole intestine prior to delamination of the tela submucosa substantially removes these contaminants and provides a preferred implantable tela submucosa tissue which is substantially free of blood and blood components as well as any other microbial organisms, pyrogens or other pathogens that may be present. In effect, this procedure is believed to substantially preserve the inherent aseptic state of the tela submucosa, although it should be understood that it is not intended that the present invention be limited by any theory.

It is also desirable that the first biomaterial 12, such as the collagenous biomaterial according to the present invention be substantially free of any antiviral agents or any antimicrobial type agents which can affect the biochemistry of the biomaterial and its efficacy upon implantation. In the past, one method of treating such tissue material is to rinse the delaminated tissue in saline and soak it in an antimicrobial agent, for example, as disclosed in U.S. Pat. No. 4,956,178. While such techniques can optionally be practiced with isolated collagenous mucosa or submucosa of the present invention, preferred processes according to the present invention avoid the use of antimicrobial agents and the like which can not only affect the biochemistry of the collagenous biomaterial but also can be unnecessarily introduced into the tissues of the patient.

As discussed above, it has been discovered that a highly pure form of an implantable tela submucosa collagen biomaterial can be obtained by first disinfecting a tela submucosa source prior to removing a purified collagen biomaterial including the tela submucosa layer, e.g. by delaminating the tela submucosa source. It has also been discovered that certain processing advantages as well as improved properties of the resultant tela submucosa layer are obtained by this process, including greater ease in removing attached tissues from the submucosa layer, and a characteristic, low contaminant profile.

Processes of the invention desirably involve first rinsing the tela submucosa source one or more times with a solvent, suitably water. The rinsing step is followed by treatment with a disinfecting agent. The disinfecting agent is desirably an oxidizing agent. Preferred disinfecting agents are peroxy compounds, preferably organic peroxy compounds, and more preferably peracids. Such disinfecting agents are desirably used in a liquid medium, preferably a solution, having a pH of about 1.5 to about 10, more preferably a pH of about 2 to about 6, and most preferably a pH of about 2 to about 4. In methods of the present invention, the disinfecting agent will generally be used under conditions and for a period of time which provide the recovery of characteristic, purified submucosa matrices as described herein, preferably exhibiting a bioburden of essentially zero and/or essential freedom from pyrogens. In this regard, desirable processes of the invention involve immersing the tissue source (e.g. by submersing or showering) in a liquid medium containing the disinfecting agent for a period of at least about 5 minutes, typically in the range of about 5 minutes to about 40 hours, and more typically in the range of about 0.5 hours to about 5 hours.

A preferred peroxy disinfecting agent is hydrogen peroxide. The concentration of hydrogen peroxide can range from about 0.05% to 30% by volume. More preferably the hydrogen peroxide concentration is from about 1% to 10% by volume and most preferably from about 2% to 5% by volume. The solution can or can not be buffered to a pH from about 5 to 9. More preferably the pH is from about 6 to 7.5. These concentrations can be diluted in water or in an aqueous solution of about 2% to about 30% by volume alcohol. Most preferably the alcohol is ethanol. The solution temperature can range from about 15 to 50° C. More preferably the solution temperature is from about 20 to 40° C. Most preferably, the solution temperature is from about 32 to 37° C. The exposure time can range from about 10 to 400 minutes. Preferably, the exposure time is from about 120 to 240 minutes. More preferably, the exposure time is from 180 to 210 minutes.

A preferred organic peroxide disinfecting agent is perpropionic acid. The concentration of perpropionic acid can range from about 0.1% to 10% by volume. More preferably the perpropionic acid concentration is from about 0.1% to 1.0% by volume and most preferably from about 0.2% to 0.5% by volume. These concentrations of perpropionic acid can be diluted in water or in an aqueous solution of about 2% to about 30% by volume alcohol. Most preferably the alcohol is ethanol. The tela submucosa tissue source can be exposed to the organic peroxide solution for periods from about 15 minutes to about 40 hours, and more typically in the range of about 0.5 hours to about 8 hours. Other peroxy disinfecting agents are suitable for use as described in "Peroxygen Compounds", S. Block, in *Disinfection, Sterilization and Preservation*, S. Block, Editor, 4th Edition, Philadelphia, Lea & Febiger, pp. 167-181, 1991; and "Disinfection with peroxygens", M. G. C. Baldry and J. A. L. Fraser, in *Industrial Biocides*, K. Payne, Editor, New York, John Wiley and Sons, pp. 91-116, 1988.

Another oxidizing disinfecting agent is chlorhexidine (1,6-di(4-chlorophenyldiguanido)hexane) in its digluconate form. The concentration of chlorhexidine digluconate can range from about 0.1% to 15% by weight. More preferably, the chlorhexidine digluconate concentration is from about 0.1% to 2% by weight and most preferably from about 0.2% to 5% by weight. The solution can or can not be buffered to a pH from about 5 to 8. More preferably the pH is from about 5.5 to 7. These concentrations can be diluted in water or in an aqueous solution of about 2% to about 20% by volume alcohol. Most preferably the alcohol is ethanol at a concentration of about 5% to 10%. The solution temperature can range from about 15 to 30° C. The exposure time can range from about 10 to 400 minutes. More preferably the exposure time is from about 30 to 60 minutes. Other chlorine agents are described in "Chlorhexidine", G. W. Denton, in *Disinfection, Sterilization and Preservation*, S. Block, Editor, 4th Edition, Philadelphia, Lea & Febiger, pp. 274-289, 1991.

In preferred preparative processes, a peracid or other disinfecting agent can be dissolved in a dilute aqueous alcohol solution, preferably wherein the alcohol has from 1 to about 6 carbon atoms, and wherein the alcohol can generally comprise from about 1% to about 30% by volume of the solution. More preferred alcohols for use in the invention are selected from the group consisting of ethanol, propanols and butanols. Ethanol is a preferred alcohol for these purposes.

When a peracid is used in the disinfection, it is preferably selected from the group consisting of peracetic acid, perpropionic acid or perbenzoic acid. Peracetic acid is the most preferred disinfecting agent. The peracetic acid is preferably diluted into about a 2% to about 10% by volume alcohol solution. The concentration of the peracetic acid can range, for example, from about 0.05% by volume to about 1.0% by volume. Most preferably the concentration of the peracetic acid is from about 0.1% to about 0.3% by volume. Hydrogen peroxide can also be used as a disinfecting agent. Alternatively, or in addition, the tela submucosa tissue source, e.g. from small intestine, can be disinfected utilizing disinfecting agents such as glutaraldehyde, formalin and the like, which are also known for their ability to introduce substantial crosslinking into collagen matrices, in contrast to the action of other disinfecting agents such as peracids which can be used to disinfect without introducing such crosslinking. Additionally, the tela submucosa source can be treated with radiation, e.g., gamma radiation, for purposes of disinfection.

Variations on the disinfection process can also include the following:

1. Intestine is treated with 0.2% peracetic acid, 5% ethanol solution at a ratio of 10:1 solution to intestine ratio by weight. Solution has a pH of 2.6. Solution and intestine are vigorously mixed for two hours.
2. Intestine is treated with 1% peracetic acid, 25% ethanol solution at a ration of 5:1 solution to intestine ratio by weight. Solution has a pH of 2. Solution and intestine are vigorously mixed for one hour.
3. Intestine is treated with 1% peracetic acid, 15% ethanol, and 10% hydrogen peroxide solution at a ratio of 5:1 solution to intestine ratio by weight. Solution and intestine are vigorously mixed for one hour.
4. Whole small intestine is rinsed four times with high purity water for 15 minutes. The intestine is then subjected to 1.5 MRAD Electron Beam radiation.
5. Whole small intestine is rinsed four times with high purity water for 15 minutes. Lengthwise along a conveyor belt, the intestine is subjected to high-intensity pulsed light which disinfects the intestine.

Following the treatment as described above, the tela submucosa layer is delaminated from its source, e.g., whole intestine, cow uterus and the like. It has been found that by following this post-disinfection-stripping procedure, it is easier to separate the tela submucosa layer from the attached tissues, e.g. at least from attached tunica muscularis tissue, as compared to stripping the tela submucosa layer prior to disinfection. Moreover it has been discovered that the resultant tela submucosa layer in its most preferred form exhibits superior histology, in that there is less attached tissue and debris on the surface compared to a tela submucosa layer obtained by first delaminating the tela submucosa layer from its source and then disinfecting the layer. Moreover, a more uniform tela submucosa tissue can be obtained from this process, and a tela submucosa having the same or similar physical and biochemical properties can be obtained more consistently from each separate processing run. Importantly, a highly purified, substantially sterile tela submucosa is obtained by this process. The stripping of the tela submucosa source is preferably carried out by utilizing a disinfected or sterile casing machine, to produce a tela submucosa which is substantially sterile and which has been minimally processed. A suitable casing machine is the Model 3-U-400 Stridhs Universal Machine for Hog Casing, commercially available from the AB Stridhs Maskiner, Götoborg, Sweden. Therefore, the measured bioburden levels are minimal or substantially zero. Of course, other means for delaminating the tela submucosa source can be employed without departing from the present invention, including for example those means well known in the art, including delaminating by hand.

It has also been discovered that more preferred processes according to the present invention, not only will eliminate or significantly reduce contaminants contained in the tela submucosa collagen biomaterial, but also will produce a tissue which exhibits no substantial degradation of physical and mechanical properties, e.g., differential porosity (i.e. wherein one side of the submucosa layer has greater porosity than the other side), and good strength, for example burst strength. Also, it has been discovered that more preferred processes do not affect the differential porosity of the tela submucosa collagen biomaterial, which ultimately affects the level of efficacy of this tissue implant. For example, the tissue is not necessarily treated with a crosslinking agent or a material that disrupts the porosity or inherent, native structure of the collagen biomaterial. Moreover, when hydrogen peroxide is employed, the biomaterial as a whole has greater porosity as well as a higher oxygen content. This helps to ensure the absence of contaminants e.g., endotoxins, pyrogens, and the like.

Preferred collagen-based matrices of the invention, preferably submucosa-containing matrices, are also characterized by the low contaminant levels set forth in Table 1 below, each contaminant level taken individually or in any combination with some or all of the other disclosed contaminant levels. The abbreviations in Table 1 are as follows: CFU/g=colony forming units per gram; PFU/g=plaque forming units per gram; µg/mg=micrograms per milligram; ppm/kg=parts per million per kilogram; and EU/g=endotoxin units per gram.

TABLE 1

| FEA-TURE | FIRST PREFERRED LEVEL | SECOND PREFERRED LEVEL | THIRD PREFERRED LEVEL |
|---|---|---|---|
| ENDOTOXIN | <12 EU/g | <10 EU/g | <5 EU/g |
| BIOBURDEN | <2 CFU/g | <1 CFU/g | <0.5 CFU/g |
| FUNGUS | <2 CFU/g | <1 CFU/g | <0.5 CFU/g |
| NUCLEIC ACID | <10 µg/mg | <5 µg/mg | <2 µg/mg |
| VIRUS | <500 PFU/g | <50 PFU/g | <5 PFU/g |
| PROCESSING AGENT | <100,000 ppm/kg | <1,000 ppm/kg | <100 ppm/kg |

Even more preferred collagen-based matrices 10 of the invention contain an endotoxin level of less than 1 EU/g, and most preferably less than 0.5 EU/g.

Purified collagen-based matrices according to the present invention can be processed in a number of ways, to provide collagenous matrices useful both in vitro and in vivo. For example, the submucosa can be configured to provide tissue grafts useful in vascular applications, e.g. as generally described in U.S. Pat. Nos. 2,127,903 and 4,902,508.

The tela submucosa of the invention possesses mechanical properties highly desirable for tissue graft materials in vascular applications, including low porosity index, high compliance, and a high burst strength. One skilled in the art will appreciate that the preferred tissue graft material will be of low enough porosity to prevent intraoperative hemorrhage and yet of high enough porosity to allow extension of a newly-developed vasa vasorum through the graft material to nourish the neointimal and luminal surface.

Tela submucosa tissue of the present invention can also be processed to provide fluidized compositions, for instance using techniques as described in U.S. Pat. No. 5,275,826. In this regard, solutions or suspensions of the tela submucosa can be prepared by comminuting and/or digesting the tela submucosa with a protease (e.g. trypsin or pepsin), for a period of time sufficient to solubilize the tissue and form substantially homogeneous solution. The submucosa starting material is desirably comminuted by tearing, cutting, grinding, shearing or the like. Grinding the submucosa in a frozen or freeze-dried state is advantageous, although good results can be obtained as well by subjecting a suspension of pieces of the submucosa to treatment in a high speed blender and dewatering, if necessary, by centrifuging and decanting excess waste. The comminuted tela submucosa can be dried, for example freeze dried, to form a powder. Thereafter, if desired, the powder can be hydrated, that is, combined with water or buffered saline and optionally other pharmaceutically acceptable excipients, to form a fluid tissue graft composition, e.g. having a viscosity of about 2 to about 300,000 cps at 25° C. The higher viscosity graft compositions can have a gel or paste consistency.

Fluidized tela submucosa of this invention finds use as an injectable heterograft for tissues, for example, bone or soft tissues, in need of repair or augmentation most typically to correct trauma or disease-induced tissue defects. The present fluidized submucosa compositions are also used advantageously as a filler for implant constructs comprising, for example, one or more sheets of tela submucosa formed into sealed (sutured) pouches for use in cosmetic or trauma-treating surgical procedures.

In one illustrative preparation, tela submucosa prepared as described herein is reduced to small pieces (e.g. by cutting) which are charged to a flat bottom stainless steel container. Liquid nitrogen is introduced into the container to freeze the specimens, which are then comminuted while in the frozen state to form a coarse tela submucosa powder. Such processing can be carried out, for example, with a manual arbor press with a cylindrical brass ingot placed on top of the frozen specimens. The ingot serves as an interface between the specimens and the arbor of the press. Liquid nitrogen can be added periodically to the tela submucosa specimens to keep them frozen.

Other methods for comminuting tela submucosa specimens can be utilized to produce a tela submucosa powder usable in accordance with the present invention. For example, tela submucosa specimens can be freeze-dried and then ground using a manual arbor press or other grinding means. Alternatively, tela submucosa can be processed in a high shear blender to produce, upon dewatering and drying; a tela submucosa powder.

Further grinding of the tela submucosa powder using a prechilled mortar and pestle can be used to produce a consistent, more finely divided product. Again, liquid nitrogen is used as needed to maintain solid frozen particles during final grinding. The powder can be easily hydrated using, for example, buffered saline to produce a fluidized tissue graft material of this invention at the desired viscosity.

To prepare another preferred fluidized material, a tela submucosa powder can be sifted through a wire mesh, collected, and subjected to proteolytic digestion to form a substantially homogeneous solution. For example, the powder can be digested with 1 mg/ml of pepsin (Sigma Chemical Co., St. Louis Mo.) and 0.1 M acetic acid, adjusted to pH 2.5 with HCl, over a 48 hour period at room temperature. After this treatment, the reaction medium can be neutralized with sodium hydroxide to inactivate the peptic activity. The solubilized submucosa can then be concentrated by salt precipitation of the solution and separated for further purification and/or freeze drying to form a protease-solubilized intestinal submucosa in powder shape.

Fluidized tela submucosa compositions of this invention find wide application in tissue replacement, augmentation, and/or repair. The fluidized submucosal compositions can be used to induce regrowth of natural connective tissue or bone in an area of an existent defect. By injecting an effective amount of a fluidized submucosa composition into the locale of a tissue defect or a wound in need of healing, one can readily take advantage of the biotropic properties of the tela submucosa. Interestingly, fluidizing SIS by comminution or enzymatic degradation does not result in any appreciable loss of biotropic activities, as shown in U.S. Pat. No. 5,275,826.

It is also possible to shape large surface area constructs by combining two or more tela submucosa segments of the invention, for instance using techniques as described in U.S. Pat. No. 2,127,903 and/or International Publication No. WO 96/32146, dated Oct. 17, 1996, publishing International Application No. PCT/US96/04271, filed 5 Apr. 1996. Thus, a plurality of tela submucosa strips can be fused to one another, for example by compressing overlapping areas of the strips under dehydrating conditions, to form an overall planar construct having a surface area greater than that of any one planar surface of the individual strips used to shape the construct. Shapes can be made by using sutures, staples, biocompatible adhesives such as collagen binding pastes, or dehydrating overlapping structures then heating the structure as described in U.S. Pat. No. 3,562,820.

The tela submucosa powder can be used alone, or in combination with one or more additional bioactive agents such as physiologically compatible minerals, growth factors, antibiotics, chemotherapeutic agents, antigen, antibodies, enzymes and hormones. Preferably, the powder-form implant will be compressed into a predetermined, three-dimensional shape, which will be implanted into the bone region and will substantially retain its shape during replacement of the graft with endogenous tissues.

Tela submucosa of the invention can also be used as a cell growth substrate, illustratively in sheet, paste or gel shape in combination with nutrients which support the growth of the subject cells, e.g. eukaryotic cells such as endothelial, fibroblastic, fetal skin, osteosarcoma, and adenocarcinoma cells (see, e.g. International Publication No. WO 96/24661 dated 15 Aug. 1996, publishing International Application No. PCT/US96/01842 filed 9 Feb. 1996. In preferred forms, the tela submucosa substrate composition will support the proliferation and/or differentiation of mammalian cells, including human cells.

The inventive tela submucosa can also serve as a collagenous biomaterial in compositions for producing transformed cells, (see, e.g., International Publication No. WO 96/25179 dated 22 Aug. 1996, publishing International Application No. PCT/US96/02136 filed 16 Feb. 1996; and International Publication No. WO 95/22611 dated 24 Aug. 1995, publishing International Application No. PCT/US95/02251 filed 21 Feb. 1995). Such compositions for cell transformation will generally include purified tela submucosa of the present invention, for example in fluidized or paste shape as described in U.S. Pat. No. 5,275,826, in combination with a recombinant vector (e.g. a plasmid) containing a nucleic acid sequence with which in vitro or in vivo target cells are to be genetically transformed. The cells targeted for transformation can include, for example, bone progenitor cells. In addition to the medicaments described above, the biomaterial may also be used as a vehicle for genetic therapy, in which exogenous nucleic acids are disposed on the graft 10. As such upon implantation, local tissue takes up the nucleic acids and thus gene transfer occurs. The process for this is described in U.S. Pat. No. 5,763,416 to Bonadio et al., the disclosure of which is expressly incorporated by reference. As such, the graft 10 can comprise a biomaterial having an extension 14, an aperture 16, and an exogenous nucleic acid disposed thereon.

In order to promote a further understanding of the present invention and its features and advantages, the following specific Examples are provided. It will be understood that these specific Examples are illustrative, and not limiting, of the present invention.

EXAMPLE 1

Thirty feet of whole intestine from a mature adult hog is rinsed with water. This material is then treated in a 0.2% by volume peracetic acid in a 5% by volume aqueous ethanol solution for a period of two hours with agitation. The tela submucosa layer is then delaminated in a disinfected casing machine from the whole intestine. The delaminated tela submucosa is rinsed four (4) times with sterile water and tested for impurities or contaminants such as endotoxins, microbial organisms, and pyrogens. The resultant tissue was found to have essentially zero bioburden level. The tela submucosa layer separated easily and consistently from the whole intestine and was found to have minimal tissue debris on its surface.

EXAMPLE 2

A ten foot section of porcine whole intestine is washed with water. After rinsing, this section of tela submucosa intestinal collagen source material is treated for about two and a half hours in 0.2% peracetic acid by volume in a 5% by volume aqueous ethanol solution with agitation. Following the treatment with peracetic acid, the tela submucosa layer is delaminated from the whole intestine. The resultant tela submucosa is then rinsed four (4) times with sterile water. The bioburden was found to be essentially zero.

EXAMPLE 3

A small section of the tela submucosa intestinal collagen material was subcutaneously implanted in a rat. Within 72 hours, significant angiogenesis was observed.

EXAMPLE 4

Two sections of small intestine are processed by differing methods. The first section is rinsed in tap water, disinfected for 2 hours in a 5% by volume aqueous ethanol solution comprising 0.2% by volume peracetic acid, pH approximately 2.6, delaminated to the tela submucosa, rinsed in purified water, divided into two samples and rapidly frozen. The second section is rinsed in tap water, delaminated to the tela submucosa, rinsed in purified water, placed in a 10% neomycin sulfate solution for 20 minutes (as described in U.S. Pat. No. 4,902,508), rinsed in purified water, divided into two samples and rapidly frozen. The four above-prepared samples are tested for bioburden and endotoxin levels. The first two samples each have bioburdens of less than 0.1 CFU/g and endotoxin levels of less than 0.1 EU/g. The second two samples have respective bioburdens of 1.7 CFU/g and 2.7 CFU/g and respective endotoxin levels of 23.9 EU/g and 15.7 EU/g.

EXAMPLE 5

Three sections of small intestine are processed by differing methods. The first is rinsed in tap water, disinfected for 2 hours in a 5% by volume aqueous ethanol solution comprising 0.2% by volume peracetic acid, pH about 2.6, delaminated to the tela submucosa, rinsed in purified water, and rapidly frozen. The second is rinsed in tap water, delaminated to the tela submucosa, rinsed in purified water, disinfected according to the methods of Example 1 in U.S. Pat. No. 5,460,962 (treatment for 40 hours in a 0.1% by volume aqueous solution of peracetic acid, buffered to pH 7.2), and rapidly frozen. The third is rinsed in tap water, delaminated to the tela submucosa, rinsed in purified water, disinfected according to the methods of Example 2 in U.S. Pat. No. 5,460,962 (treatment in 0.1% by volume peracetic acid in high salt solution, buffered to pH 7.2), and rapidly frozen. All three samples were tested for endotoxins. The endotoxin levels were <0.14 EU/g for the first sample, >24 EU/g for the second sample, and >28 EU/g for the third sample.

EXAMPLE 6

Two sections of porcine small intestine were infected with $7 \times 10^6$ plaque forming units (PFU) of virus. Both were exposed to a 0.18% peracetic acid, 4.8% aqueous ethanol solution at a nine-to-one weight ratio of solution to material. A first sample was immersed in this solution for 5 minutes; the second was immersed for 2 hours. The material processed for 5 minutes exhibited 400 PFU per gram of material. The material processed for 2 hours exhibited zero PFU per gram of material.

EXAMPLE 7

Purified tela submucosa, prepared as described herein, was tested to determine its nucleic acid content. Four samples of material weighing 5 mg each were subjected to DNA/RNA extraction as detailed in the DNA/RNA Isolation Kit by Amersham Lifescience Inc., Arlington Heights, Ill. Nucleic acid quantitation was performed by spectrophotometric determination of solution optical densities at 260 nm and 280 nm. The average nucleic acid content was 1.9±0.2 mg per milligram of material.

Small intestinal submucosa, prepared as described by U.S. Pat. No. 4,902,508, was tested to determine its nucleic acid content. Four samples of material weighing 5 mg each were subjected to DNA/RNA extraction as detailed in the DNA/RNA Isolation Kit by Amersham. Nucleic acid quantitation was performed by spectrophotometric determination of solution optical densities at 260 nm and 280 nm. The average nucleic acid content was 2.4±0.2 mg per milligram of material.

EXAMPLE 8

Sections of tela submucosa prepared according to the methods described herein were sent to an independent testing laboratory (NamSA, Inc., Northwood, Ohio) for biocompatibility testing as described in the standard ISO 10993. The samples were tested for USP Acute Systemic Toxicity, USP Intracutaneous Toxicity, Cytotoxicity, LAL Endotoxin, material-mediated Pyrogenicity, Direct Contact Hemolysis, and Primary Skin Irritation. The samples passed all tests, indicating that the material is biocompatible.

EXAMPLE 9

Using the procedure set forth in U.S. Pat. No. 5,460,962, two samples were analyzed. The first Kemp sample indicated an endotoxin level greater than 24 endotoxin units per gram and the second Kemp sample indicated an endotoxin level greater than 28 endotoxin units per gram. Thus, when using the procedure set forth in Kemp '962, the endotoxin levels fall outside the biocompatibility-levels.

EXAMPLE 10

Using the procedures set forth in U.S. Pat. Nos. 4,902,508 and 5,372,821 issued to Badylak, the endotoxin level shown ranges as high as 23.9 endotoxin units per gram of sample. This falls outside the permissible range and thus does not meet the criteria of biocompatibility as defined above. The invention, prepared in the above prescribed manner of disinfection first then delamination, was observed to have an endotoxin level of less than 12 endotoxin units per gram, and more particularly, reported an endotoxin level of less than 5 endotoxin units per gram. Thus, the material of the present invention is biocompatible as defined above.

With particular reference to FIGS. 1 and 2, shown in FIG. 1 is the graft 10 in partially folded condition, and shown in FIG. 2 is the graft 10 in flat sheet form. Graft 10 comprises a first biomaterial 12 with at least one extension 14, with most likely a plurality of extensions 14. Extension 14 includes a tab, a projection, an insertion, or a male portion of a lock. Also provided on graft 10 first biomaterial 12 is at least one aperture 16, with most likely a plurality of apertures 16. Aperture 16 includes a slit, a hole, an orifice, or a receiving member. Extension 14 is generally shaped so that extension 14 can be inserted into aperture 16. Extension 14 need not, however, be the same size of aperture 16. Extension 14 need only be shaped in such a way as to insert into aperture 16. To this end, extension 14 may be rectangular, mushroom shaped, or club shaped. In addition, the extension 14 and aperture 16 include the well-known male-female locking mechanisms.

In one embodiment of the invention, extension 14 is larger or wider that aperture 16. In this manner, the surplusage of extension 14 material fitting through or in aperture 16 causes the extension 14 to not come out or get pulled out of aperture 16. In this regard extension 14 does not get pulled out of aperture 16 causing extension 14 to be relatively "locked" into place.

Extension 14 is moved into proximity of aperture 16, usually by folding the fist biomaterial 12 sheet in direction 17. That is, when the sheet is flat lying on a table, the inside wall 18 of graft 10 is the surface facing up, thus forming inside wall surface 20. The exterior surface 22 of extension 14 is the surface adjacent to the table. As such, graft 10 is formed by grasping the sides and bringing them into proximity of each other direction 17. As such, extension 14 has a leading edge 24 and leading edge 24 inserts into aperture 16. If a series of extensions 14 are present; then selective extensions 14 can be inserted into one aperture 16 or a plurality of apertures 16.

Figure 3:
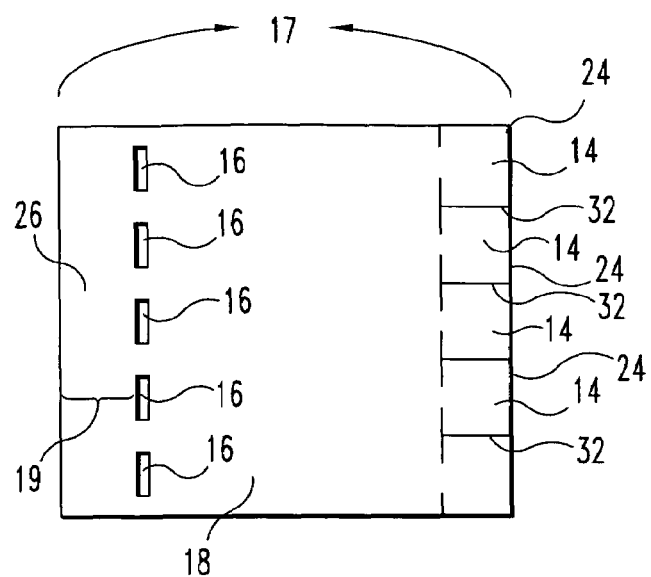
FIGS. 3 and 3A represent other embodiments of the present invention including retainers.

As further shown in FIGS. 2 and 3, aperture 16 can be along the edge of the sheet or at some distance 19, an extra amount or surplus material 26 is formed. This material can be the same material as the sheet or can be a second material 26.

Figure 4:
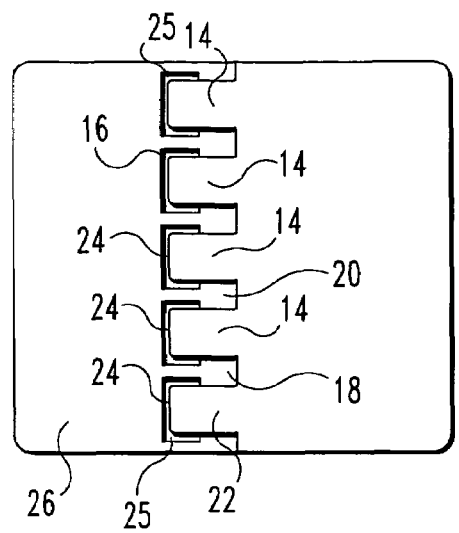
FIG. 4 represents extensions inserted into the apertures.

As shown in FIG. 4, leading edge 24 is inserted into aperture 16. As the sheet lies flat on the table, the inside wall 18 is partially seen in between the plurality of extensions 14. The exterior surface 22 of extension 14 is on the top side or opposite side to the inside wall 18.

Figure 5:
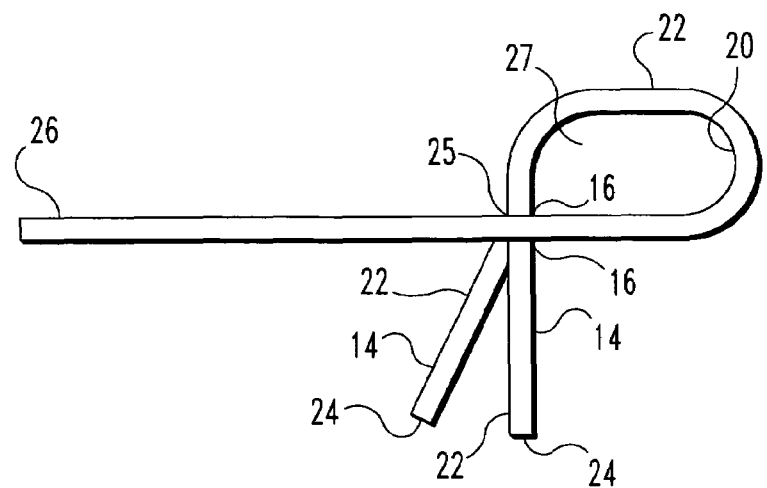
FIG. 5 represents a side view of the extensions inserted into the apertures, showing multiple extensions.
Figure 6:
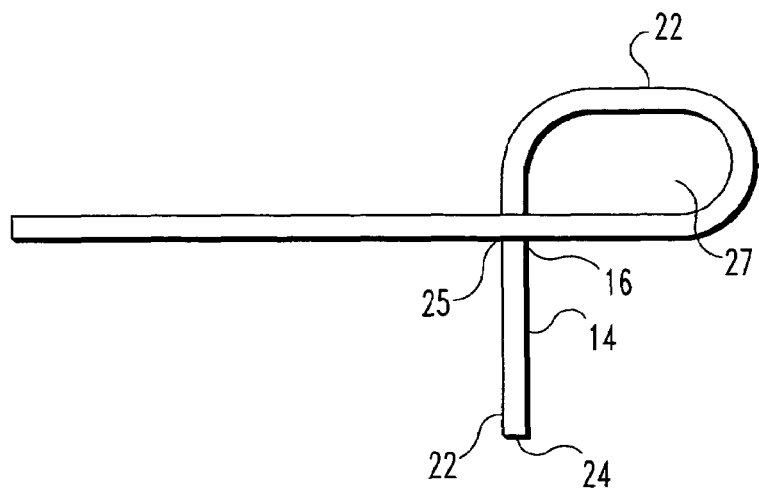
FIG. 6 represents a side view of one extension inserted into the aperture.

As shown in FIGS. 5 and 6, leading edge 24 of extension 14 is inserted into and through aperture 16. As leading edge 24 is pulled through the aperture, a tube is created at that point, thus creating lumen 27. As successive extensions 24 are pulled through the aperture, the rest of the tube is created, creating an extended lumen 27. The "seam" resembles the familiar dovetail joint characteristically found in wood-working furniture assembly.

Figure 7:
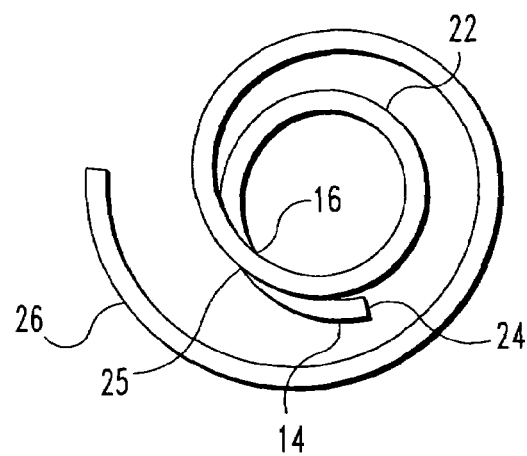
FIG. 7 represents a side view of an intermediate layer disposed over the aperture.

As shown in FIG. 7, as the successive extensions 14 are pulled through the apertures 16, the surplus material 26 can be folded or rolled around the newly forming tube. In this regard, the surplus material 26 can be folded or rolled in such a manner as to cover or overlap the aperture 16 extension 14 junction 25. This way, upon completion of the graft 10, surplus material 26 will provide a seal over the aperture 16, and more particularly, over junction 25. The more times that surplus material 26 can wrap around the tube, the greater the structural integrity that is present. In addition, the existence of seepage or leakage is dramatically reduced.

Figure 8:
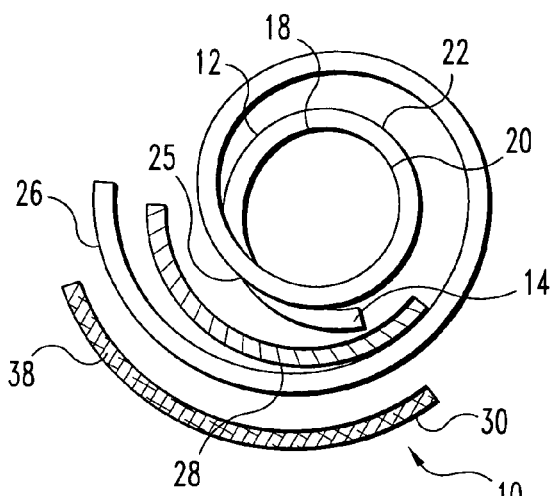
FIG. 8 represents side view of an intermediate layer disposed between the aperture and the surplus biomaterial.

FIG. 8 shows another embodiment of the present invention. To provide extra leak protection or to provide medicaments, an intermediate layer 28 can be strategically placed over the aperture 16- extension 14 junction 25. The intermediate layer 28 or outer layer 30 comprises at least one of the submucosal tissue, mucosal tissue, serosal tissue, collagen, partially collagenous biomaterial, elastin, polytetraflouroethylene, polyester, stainless steel, DACRON (R), ORLON (R), FORTISAN (R), nylon, polypopylene, polyglatin 910, polyglycolic acid, pericardium, dura tissue, facia lata, a biocompatible material, polymers, co-polymers, polypyrramidole, a synthetic material, and any combination or part thereof. Thus, in its simplest but non exclusive embodiment, the graft 10 can comprise a biological tissue for the initial sheet, a biological tissue for the surplus material 26, a biological tissue for the intermediate layer 28, and a biological tissue for outer layer 30. However, any combination of materials may be used. For example, the initial sheet of first biomaterial 12 and surplus material 26 may comprise biological tissue, the intermediate layer 28 may comprise DACRON (R), and the outer layer 30 may comprise a second or different biological tissue. Therefore, specifically contemplated is that the graft 10 may include at least 4 types of materials. Also, it is possible to include a plurality of various layers as outer layers 30 to vary the composition, structural integrity, therapeutic value, or the like. For example, if long term medication is needed in the area, intermediate layer 28 may be treated with medicaments to provide a long term application. Similarly, outer layer 28 may be treated with medicaments to facilitate treatment to the adjacent or systemic tissues. In addition, any layer may completely or partially surround the graft 10, or completely or partially surround any inner layers. As mentioned herein, any layer, including the first biomaterial 12 itself, may be treated with medicaments to provide therapy to an afflicted area.

Figure 9:
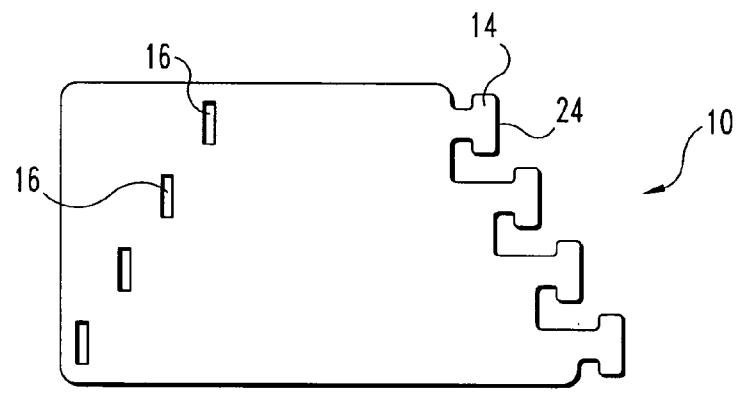
FIG. 9 represents another embodiment of the present invention.

FIG. 9 shows another embodiment of the present invention. Apertures 16 need not be in a line equidistant from the sheet edge. In fact, the apertures may be staggered or randomly placed to provide a varying shape or lumen size of the overall graft 10. By calculating the various configurations, one could create a tube with a gradually increasing or decreasing lumen size.

Figure 10:
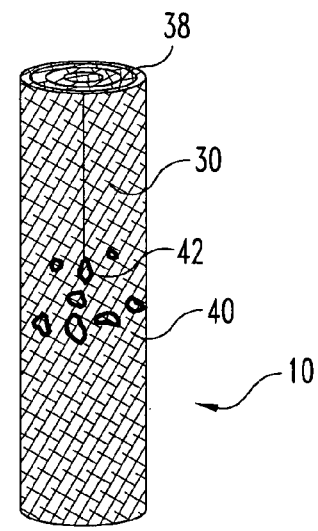
FIG. 10 represents an outer layer disposed over the graft construct.

FIG. 10 shows another embodiment of the present invention. In this case, graft 10 is provided with a woven outer layer 30. This outer layer 30, as with intermediate layer 28 (as shown in FIG. 8), comprise a biocompatible material such as submucosal tissue, mucosal tissue, serosal tissue, collagen, partially collagenous biomaterial, polytetraflouroethylene, polyester, stainless steel, DACRON(R), ORLON(R), FORTISAN(R), nylon, polypropylene, polyglactin 910, polyglycolic acid, pericardium, dura tissue, facia lata, a biocompatible material, polymers, polypyrramidole, co-polymers, a synthetic material, and any combination or part thereof.

Figure 11:
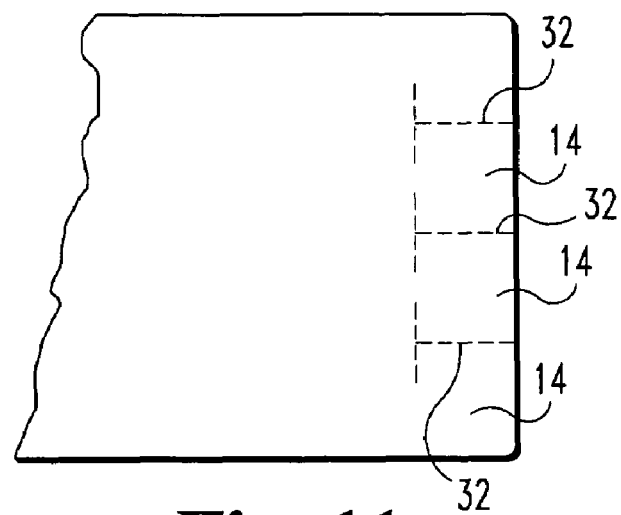
FIG. 11 represents a series of retainers on a graft of the invention.

FIG. 11 shows a section of the extensions 14. This embodiment particularly uses a retainer 32 to relatively "lock" the extension 14 into place after insertion into aperture 16. In this embodiment of the invention, the retainer 32 is actually part of the initial sheet. However, specifically contemplated are other retainers 32, such as locks, sutures, adhesives, staples, suture wire on the ablumenal side or other well known methods for creating a retainer 32. Any method of locking two sections of tissue together is specifically contemplated herein. In this non-limiting embodiment, the dotted lines of FIG. 11 indicate where the sheet is cut to form each extension 14. Thus the "locking" mechanisms are not entirely within the lumen.

Figure 12:
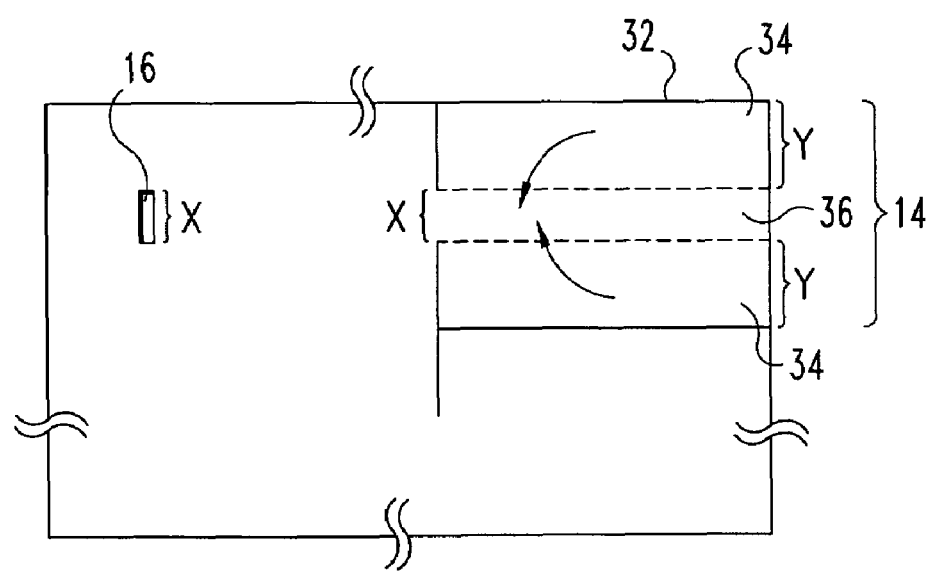
FIG. 12 provides a cut-out representing a single retainer of the invention.

FIG. 12 shows a partial section of one extension 14. To form a retainer 32, extension 14 is folded along the dotted lines in the direction shown to create a partial retainer 34. The extension 14 has a central extension 36, the central extension having a width designated X. Across the sheet is aperture 16, with aperture 16 having a width of X also. However, the widths need not be the same. When extension 14 is folded along the dotted lines shown to create width X of central extension 36, it facilitates insertion into aperture 16. When extension 14 is pulled through the aperture 16, the user can then unfold each partial retainer 34. Since each partial retainer has a width Y, the combined widths of X+Y+Y is greater than width X of the aperture 16. Thus, the extension 14 cannot easily be pulled back through the aperture 16 into the unfolded sheet configuration. Similarly, retainer 32 comprises adhesives, partial retainers, sutures, staples, or any other structure capable of securing extension 14 such that it retards the removal of extension 14 from, or through, the aperture 16.

Figure 13:
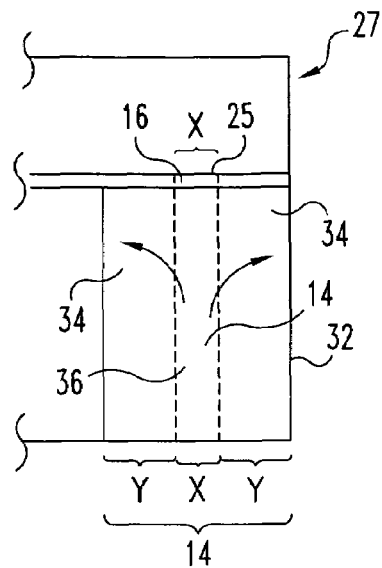
FIG. 13 represents a retainer inserted through a corresponding aperture in a graft of the invention.

FIG. 13 shows the unfolded position of extension 14, partial retainers 34, and forming the retainer 32. In this regard, the arrows indicate that each partial retainer 34 is unfolded. Evidently, the width of aperture 16 (designated as X) is the same as the width of the central extension 36 (also designated as X), but the width of extension 14 is X+Y+Y and thus, extension 14 will not easily be pulled out of aperture 16. However, the width of extension 14 need not be the same as the width of aperture 16.

Returning now to FIG. 8, once the graft 10 is made with intermediate layers 28 or outer layers 30, where appropriate, the graft 10 is then treated. Treatment includes freeze drying the graft 10. By freeze drying the graft 10, the layers are pressed further together thus providing extra leakage protection and increased structural integrity. The problem associated with other grafts made from sheets is that the inner seam on the lumenal surface 18, 20 often "hangs" down or protrudes into the lumen. That is, the layers begin to peel away and separate from each other. This poses a serious problem as a potential source of thrombogenesis. However, the present invention solves this problem by providing an "interrupted" or discontinuous seam in the lumen 27. In addition, after freeze drying the interface is sealed. Microscopic examination provides no visible evidence of the extensions 14, the apertures 16, or the junction 25. This is because the interface consists of adjacent extensions and apertures engaging each other. Thus, the graft 10 is more impermeable to leakage and provides better protection. It reduces the thrombogenesis since nothing exists to hang down into the lumen 27.

Other embodiments include using a multi-laminate sheet with which to start. For example, several collagen sheets may be used to increase structural integrity. In another example, multiple mucosal sheets can be used, as described in U.S. Pat. No. 5,885,619 to Patel et al., the disclosure of which is expressly incorporated by reference; or described in U.S. Pat. No. 5,755,791 to Whitson et al., the disclosure of which is expressly incorporated by reference.

Returning now to FIGS. 8 and 10, yet another embodiment of the present invention includes a marker 38. Marker 38 is used to initially mark the location of the junction 25. In this regard, during the manufacturing process, the marker 38 is visible and will indicate to the user the location of junction 25.

In yet another embodiment of the present invention, the graft or any individual constituent thereof may also contain a drug or chemical coating 40. For example, any layer or constituent thereof may contain a heparin coating to prevent thrombosis. In yet another embodiment of the present invention, the graft can be made radiographically visible by either making the retainer or a marker radiovisible, or making the graft radiovisible via heavy metal powders 42, such as tantalum or barium.

Figure 3A:
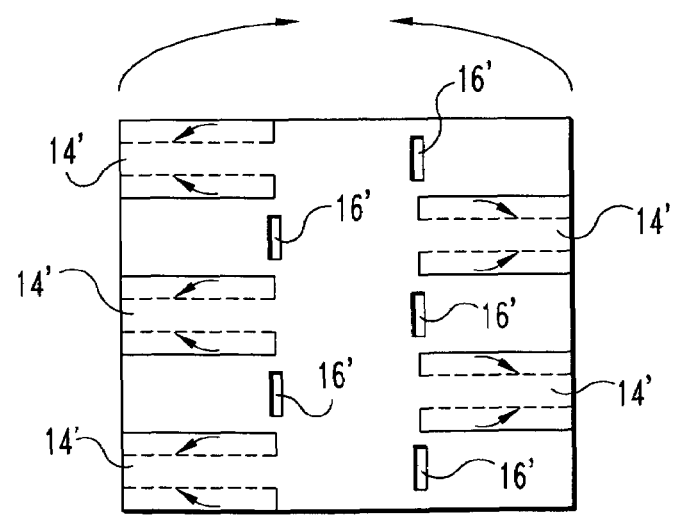

With reference now to FIG. 3A, shown is another embodiment of the present invention. Graft 10' shown in FIG. 3A is similar to the graft shown in FIG. 3, except that extensions 14' and apertures 16' occur on alternating sides of the sheet. Graft 10' is also similarly assembled into tube form, except that the folding of the extensions 14' (inwardly along dotted lines as indicated by arrows) and their insertion into corresponding apertures 16' can be carried out in alternating fashion and in alternating directions as the tube is assembled.

Figure 14:
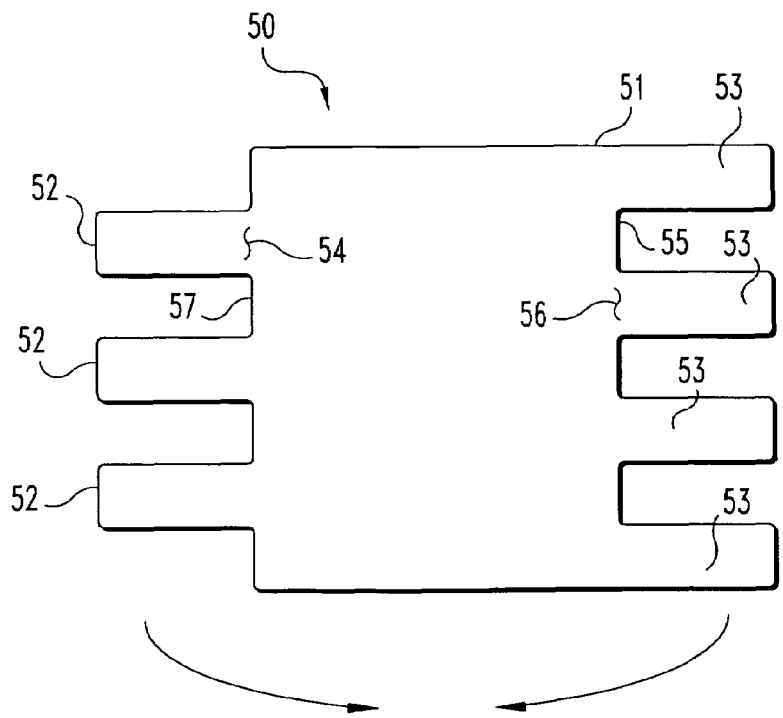
FIGS. 14-18 represent additional graft constructs of the invention.

Shown in FIG. 14 is another embodiment of the invention. Graft 50 for forming a tubular structure is formed from a sheet of biomaterial or other similar biocompatible material that includes extensions 52 offset with respect to and configured to interleave with extensions 53 occurring on the opposite side of graft 50. In this fashion, seams will be formed at the contact points of non-edge portions 54 of extensions 52 and edge portions 55 occurring between extensions 53 on the opposite side of graft 50, and at the contact points of non-edge portions 56 of extensions 53 and edge portions 57 occurring between extensions 52. In this manner, multiple, relatively smaller seam structures will be presented on the inner lumen wall of the assembled tubular graft 50. As will other grafts on the invention, extensions 52 and 53 may optionally be of sufficient length to extend around the circumference of the assembled tube at least one time so as to overlap the multiple longitudinal seams created at the contact of portions 54 and 55, and portions 56 and 57, respectively. As in other constructs of the invention, a suitable biocompatible and/or bioresorbable bonding agent may be applied to surfaces of extensions 52 and 53 or in other locations on the tube to facilitate integrity of the tube, and/or attachments of the layers may be achieved by crosslinking or other suitable methods.

Figure 15:
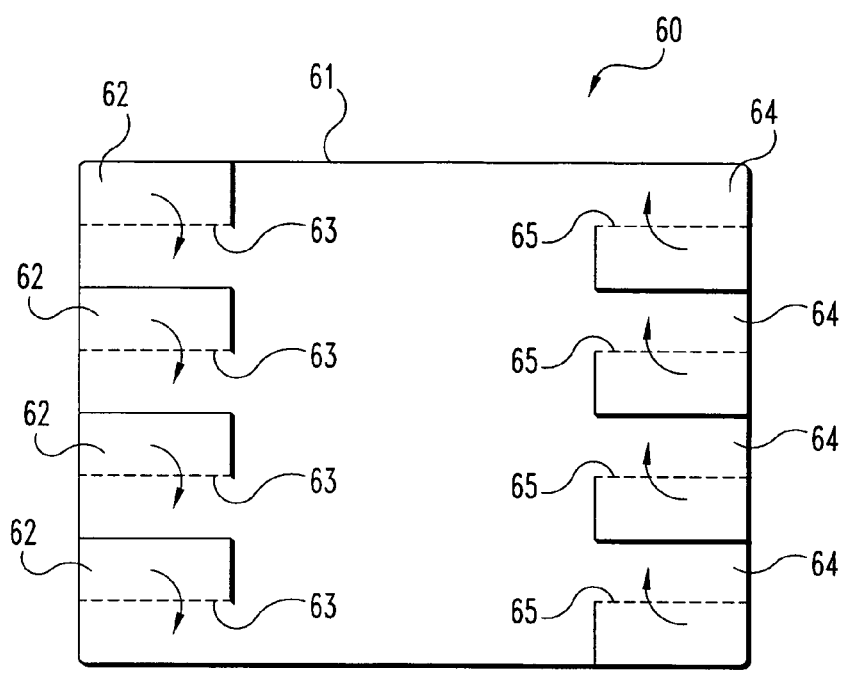
Figure 16:
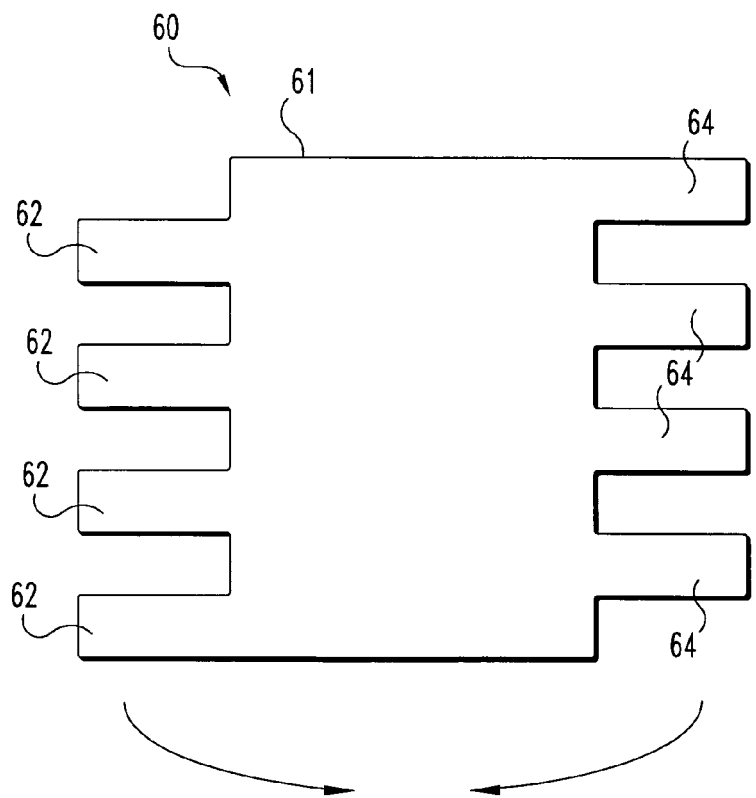

FIGS. 15 and 16 illustrate another embodiment of the invention. Graft 60 is somewhat similar in design to graft 50 of FIG. 14, except that sheet 61 of biomaterial or other similar biocompatible material has extensions 62 and 64 formed by appropriate cuts in the sheet so as to configure to interleaving extensions upon folding each extension atop itself (e.g. by folding along dotted lines 63 and 65 in FIG. 15 in the direction of the arrows). In this fashion, a construct having folded extensions 62 and 64 configured to interleave as folded is created (see FIG. 16), which can then be assembled to a tube similar to graft 50 of FIG. 14. However, after interleaving the extensions 62 and 64, they may be unfolded so as to create an overlapping set of interleaved extensions, providing for example additional overlapped surface area for bonding, crosslinkage or other attachment, and additional resistance to separation.

Figure 17:
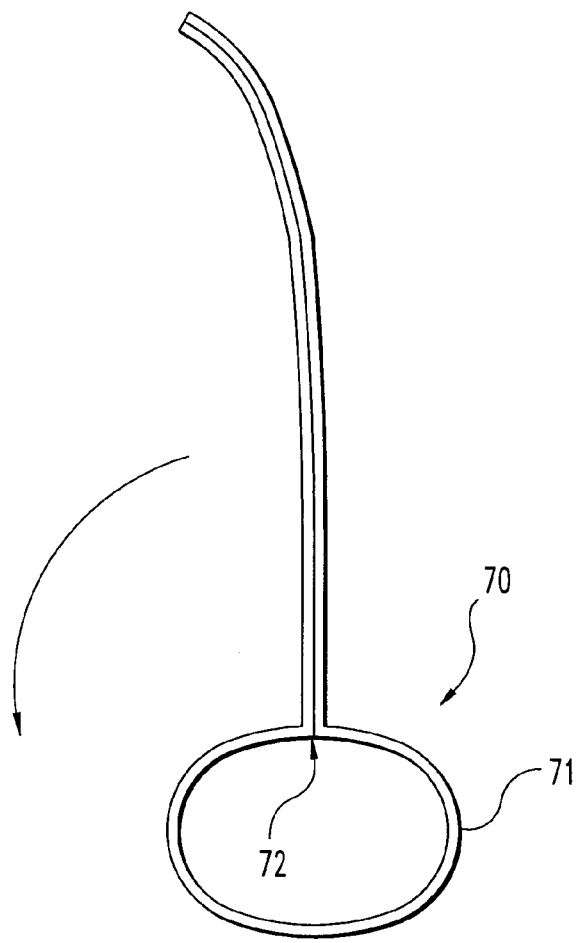
Figure 18:
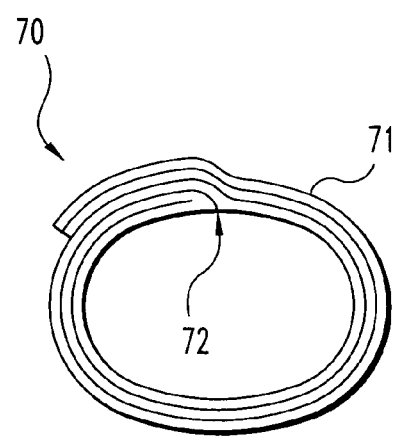

FIGS. 17 and 18 show another embodiment of the invention, in which a butt joint is utilized to create a tubular graft having a lumen wall free of any seam edge. In particular, tubular graft 70 formed especially of a biomaterial such as a collagenous sheet 71, is formed by configuring the sheet to a tube and creating a butt joint 72 to create a fluid-tight seal of the tube. Butt joint 72 is created by contact between portions of the same side of the sheet 71 and forms a longitudinal seam along the tube, but presents no edge of the original sheet. Butt joint 72 can be created using any suitable bonding or other attachment method, including for example the use of dehydration bonding (e.g. in the case of a collagenous material), a biocompatible and/or bioresorbable bonding agent, crosslinking, or the like. The biomaterial sheet may be of sufficient size to provide a length of surplus sheet which can be wrapped about the formed tube (e.g. in the direction of arrow, FIG. 17) so as to overlap the butt joint 72 at least once as illustrated in FIG. 18 or multiple times if desired. Further, additional layers of material may be provided around graft 70 to form a finished construct if desired. For example, additional layers of biomaterial may be provided and/or a tube of synthetic material as described herein may be provided around the outside of graft 70 in forming the finished tubular construct. Graft constructs having one or more butt joints creating a lumen seal can be advantageous, for example, where the sheet starting material has a sidedness, wherein presentation of one side of the material in the lumen (e.g. at an edge or upon partial detachment of a seam) of the graft is desirably avoided. For example, an isolated collagenous layer having differing physical or chemical properties on one side as compared to the other, for example small intestinal submucosa, may be used with preference with a certain side forming the lumen of the graft (e.g. the luminal side in the case of small intestinal submucosa), and the other side (e.g. abluminal side) occurring as the outer wall. In the case of a butt jointed tubular graft, only additional amounts of the originally-presented side of the sheet will potentially be exposed to the lumen of the graft. For example, in a butt-jointed tubular graft having a lumen formed of the luminal side small intestinal submucosa, no edge of the submucosa will be exposed to the lumen, and only additional luminal side portions of the submucosa (and not abluminal portions) would be exposed to the lumen of the tubular graft if some detachment of the seam occurred.

As discussed herein, tubular grafts of the invention may have layers, for example biomaterial layers such as collagenous layers, attached to one another to facilitate integrity of the construct. Attachment of layers may be achieved for example utilizing dehydration bonding of the layers (e.g. with freeze or vacuum drying), crosslinking with suitable crosslinking agents such as glutaraldehyde, formaldehyde, or the like, and/or using resorbable or non-resorbable biocompatible bonding agents such as fibrin glue, cyanoacrylates, chitin or chitosan based bonding agents, elastin containing bonding agents, or any combination thereof. Other techniques such as suturing may also be used alone or in combination with other attachment methods.

Graft constructs of the invention may be terminally sterilized using well known sterilization techniques such as radiation, ethylene oxide, or gas plasma.

Since the graft is intended to be a medical device, the graft will likely be packaged in some sterile packaging or packaged then terminally sterilized. Thus, the medical device may comprise a graft construct identified above, including a package with the package and graft being terminally sterilized.

The compositions and methods disclosed herein are only intended to be examples of the present invention. It will be apparent to those skilled in the art that modifications may be made without undue experimentation and it is contemplated that any of these modifications are within the scope of the appended claims. All publications cited herein are indicative of the level of skill possessed by those working in the art and each such publication is hereby incorporated by reference in its entirety.

We claim:
1. A medical device, comprising:
a) a first compliant collagenous biomaterial;
b) the first compliant collagenous biomaterial having an aperture extending therethrough;
c) the first compliant collagenous biomaterial also having an extension;
d) wherein the extension is shaped to be inserted into the aperture, has a width greater than a maximum width of said aperture, and is foldable for receipt through said aperture;
e) a second biocompatible material disposed on the first biomaterial; and
f) wherein an intermediate layer is disposed under the second biocompatible material.

2. The medical device of claim 1, wherein at least one of the second biocompatible material and intermediate layer comprises at least one of a submucosal tissue, mucosal tissue, collagen, partially collagenous biomaterial, and intermediate layer comprises at least one of a submucosal tissue, mucosal tissue, collagen, partially collagenous biomaterial, polytetraflouroethylene, polyester, stainless steel, DACRON, ORLON, FORTISAN, nylon, polypropylene, polyglactin 910, polyglycolic acid, pericardium, dura tissue, facia lata, a biocompatible material, polymers, co-polymers, a synthetic material, and any combination or part thereof.

3. The medical device of claim 1, wherein said biomaterial comprises a collagenous extracellular matrix material.

4. The medical device of claim 3, wherein the collagenous extracellular matrix comprises submucosal tissue.

5. The medical device of claim 3, wherein the collagenous extracellular matrix material is porcine.

6. A medical device, comprising:
a) a compliant, sealed tube configured as a leak-resistant vessel graft, the tube having a lumen extending therethrough, the tube formed from a sheet of collagenous biomaterial having a first side forming a surface of said lumen and a second side forming an external surface of said tube;
b) wherein the sheet of collagenous biomaterial defines a plurality of extensions and a plurality of apertures, with each of the plurality of apertures providing an opening extending through the sheet of collagenous biomaterial;
c) wherein each one of said plurality of extensions has a first extension portion received through a corresponding one of said plurality of apertures so as to overlie an underlying layer of material, wherein a surface of said first extension portion conforms and is bonded to the underlying layer of material by one or more of dehydrothermal bonding, crosslinking, or bonding with a resorbable or non-resorbable biocompatible bonding agent; and
d) wherein at least one of the plurality of extensions is larger than at least one of the plurality of apertures.

7. A medical device, comprising:
a) a compliant, sealed tube configured as a leak-resistant vessel graft, the tube having a lumen extending therethrough, the tube formed from a sheet of biomaterial having a first side forming a surface of said lumen and a second side forming an external surface of said tube;
b) wherein the sheet of biomaterial defines a plurality of extensions and a plurality of apertures, with each of the plurality of apertures providing an opening extending through the sheet of biomaterial;
c) wherein each one of said plurality of extensions has a first extension portion received through a corresponding one of said plurality of apertures so as to overlie an underlying layer of material, wherein a surface of said first extension portion conforms and is bonded to the underlying layer of material by one or more of dehydrothermal bonding, crosslinking, or bonding with a resorbable or non-resorbable biocompatible bonding agent;
d) wherein a second biocompatible material is disposed on the tube; and
e) wherein an intermediate layer is disposed under the second biocompatible material.

8. The medical device of claim 7, wherein the intermediate layer comprises at least one of a submucosal tissue, mucosal tissue, collagen, partially collagenous biomaterial, polytetrafluoroethylene, polyester, stainless steel, DACRON, ORLON, FORTISAN, nylon, polypropylene, polyglactin 910, polyglycolic acid, pericardium, dura tissue, facia lata, a biocompatible material, a synthetic material, polymers, co-polymers, and any combination or part thereof.

9. The medical device of claim 7, wherein each one of said plurality of extensions also includes a retainer.

10. A method of creating a tube, comprising the steps of:
a) forming at least one extension and at least one aperture on a sheet of collagenous biocompatible material;
b) inserting the at least one extension into the at least one aperture so as to form a tube;
c) engaging the at least one extension with the at least one aperture, wherein said engaging includes positioning a portion of the at least one extension through the at least one aperture so as to position said portion overlapping an underlying layer of the sheet of collagenous biocompatible material, wherein a surface of said portion conforms to the underlying layer of the sheet of collagenous biomaterial; and
d) bonding the surface of said portion to the underlying layer of the sheet of collagenous biocompatible material, wherein said bonding comprises one or more of dehydrothermal bonding, crosslinking, or bonding with a resorbable or non-resorbable biocompatible bonding agent.

11. The method of creating a tube of claim 10, wherein the steps further includes the step of disposing an intermediate layer on the tube.

12. The method of creating a tube of claim 11, wherein the steps further includes the step of disposing an outer layer on the intermediate layer.

13. The method of creating a tube of claim 10, wherein said bonding comprises crosslinking.

14. The method of claim 10, wherein said sheet of collagenous biocompatible material comprises a collagenous extracellular matrix material.

15. The method of claim 14, wherein the collagenous extracellular matrix material comprises submucosal tissue.

16. The method of claim 15, wherein the submucosal tissue is porcine.

17. A medical device, comprising:
a compliant, sealed tube formed from a sheet of collagenous biomaterial, the tube having a lumen having a lumen wall and configured as a leak-resistant vessel graft; said lumen wall free from any continuous seam edge traversing the entire length of the tube, and said lumen wall including at least one multi-layer region formed by an extension having a surface that conforms and is bonded to the underlying layer of said sheet of biomaterial by one or more of dehydrothermal bonding, crosslinking, or bonding with a resorbable or non-resorbable biocompatible bonding agent;
wherein the lumen wall presents a plurality of longitudinal seam edges;

wherein said seams are formed by intersections of edge portions of said sheet of biomaterial and non-edge portions of said sheet of biomaterial; and wherein said edge portions are formed at a perimeter of said sheet of biomaterial.

18. The medical device of claim 17, wherein said tube comprises a plurality of interleaving extensions of said biomaterial.

19. The medical device of claim 17, wherein the collagenous biomaterial is porcine.

20. A medical device, comprising:

a compliant, sealed tube formed from a sheet of biomaterial comprising submucosal tissue, the tube having a lumen having a lumen wall and configured as a leak-resistant vessel graft; said lumen wall free from any continuous seam edge traversing the entire length of the tube, and said lumen wall including at least one multi-layer region formed by an extension having a surface that conforms and is bonded to the underlying layer of said sheet of biomaterial by one or more of dehydrothermal bonding, crosslinking, or bonding with a resorbable or non-resorbable biocompatible bonding agent; and wherein said tube comprises a seam formed by a butt joint.

21. The medical device of claim 20, wherein the submucosal tissue is porcine.

* * * * *